(12) United States Patent
Ali et al.

(10) Patent No.: US 8,329,758 B2
(45) Date of Patent: Dec. 11, 2012

(54) SKIN SANITIZING ANTIMICROBIAL ALCOHOLIC COMPOSITIONS

(75) Inventors: Yusuf Ali, Hudson, OH (US); Ronald A. Barnhart, Mogadore, OH (US); Mojgan Cline, Copley, OH (US)

(73) Assignee: GOJO Industries, Inc., Akron, OH (US)

( * ) Notice: Subject to any disclaimer, the term of this patent is extended or adjusted under 35 U.S.C. 154(b) by 0 days.

(21) Appl. No.: 12/138,483

(22) Filed: Jun. 13, 2008

(65) Prior Publication Data

US 2008/0249187 A1  Oct. 9, 2008

Related U.S. Application Data

(62) Division of application No. 10/068,633, filed on Feb. 5, 2002, now abandoned.

(51) Int. Cl.
*A61K 47/30* (2006.01)
*A61K 31/00* (2006.01)
*A61K 31/045* (2006.01)

(52) U.S. Cl. .......................... 514/772.3; 514/1; 514/724
(58) Field of Classification Search .................. None
See application file for complete search history.

(56) References Cited

U.S. PATENT DOCUMENTS

| | | | |
|---|---|---|---|
| 2,798,053 A | 7/1957 | Brown | |
| 3,133,865 A | 5/1964 | Richardson et al. | |
| 3,293,127 A | 12/1966 | Beck | |
| 4,143,141 A | 3/1979 | Ensminger et al. | |
| 4,478,853 A | 10/1984 | Chaussee | |
| 4,775,524 A | 10/1988 | Blythin | |
| 4,775,529 A | 10/1988 | Sequeira et al. | |
| 4,863,969 A | 9/1989 | Bollag | |
| 4,956,170 A | 9/1990 | Lee | |
| 4,970,220 A | 11/1990 | Chaussee | |
| 5,013,545 A | 5/1991 | Blackman et al. | |
| 5,098,717 A | 3/1992 | Blackman | |
| 5,167,950 A * | 12/1992 | Lins ................................. | 424/47 |
| 5,563,292 A | 10/1996 | Shih et al. | |
| 5,661,119 A | 8/1997 | Hersh et al. | |
| 5,747,021 A * | 5/1998 | McKenzie et al. .............. | 424/73 |
| 5,750,579 A * | 5/1998 | Kamishita et al. ......... | 514/772.6 |
| 5,853,710 A * | 12/1998 | Dehan et al. .................... | 424/73 |
| 5,951,993 A | 9/1999 | Scholz et al. | |
| 5,976,566 A | 11/1999 | Samour et al. | |
| 6,093,410 A | 7/2000 | Peffly et al. | |
| 6,165,457 A | 12/2000 | Midha et al. | |
| 6,204,230 B1 | 3/2001 | Taylor et al. | |
| 6,228,385 B1 * | 5/2001 | Shick ............................. | 424/419 |
| 6,333,039 B1 * | 12/2001 | Fendler et al. ................ | 424/401 |
| 6,846,846 B2 | 1/2005 | Modak et al. | |

OTHER PUBLICATIONS

BF Goodrich Tech.Disclosure, Neutralizing carbopol and Pemulen Polymers in Aquous and hydroalcoholic systems, 1998, 3 pages.*
Jones, Antimicrobial action of acetylsalicylic acid. II. Further studies, J Am Osteopath Assoc. Jun. 1971;70(10), title page printed from http://www.ncbi.nlm.nih.gov/pubmed/5207167, 1 page.*
Al-Bakri et al., The assessment of the antibacterial and antifungal activities of aspirin, EDTA and aspirin-EDTA combination and their effectiveness as antibiofilm agents, J Appl Microbiol. Jul. 2009;107(1):280-6. Epub Mar. 10, 2009, 1 page, Abstract only.*
B.F. Goodrich technical disclosure TDS-237, "Neutralizing Carbopol™ and Pemulen™ in Aqueous and Hydroalcoholic Systems." (1998).

* cited by examiner

*Primary Examiner* — Sreeni Padmanabhan
*Assistant Examiner* — Gigi Huang
(74) *Attorney, Agent, or Firm* — Renner, Kenner, Greive, Bobak, Taylor & Weber

(57) ABSTRACT

This invention relates to an antimicrobial skin sanitizing composition for disinfecting skin, and particularly, hands. The composition contains at least 60 percent of an aliphatic alcohol having from 1 to 4 carbon atoms, from about 0.1 to about 5 weight percent of a thickening agent, and an effective amount of a GRAS or amino acid neutralizer to neutralize the thickening agent.

1 Claim, No Drawings

SKIN SANITIZING ANTIMICROBIAL ALCOHOLIC COMPOSITIONS

This Application is a divisional of patent application Ser. No. 10/068,633, filed on Feb. 5, 2002 now abandoned.

TECHNICAL FIELD

This invention relates to an antimicrobial skin sanitizing composition for disinfecting skin, and particularly, hands. The composition is high in alcohol content and employs a neutralizing agent for the thickener that is affirmed by the Food and Drug Administration (FDA) as being Generally Recognized As Safe (GRAS) under 21 CFR 184 as a direct food substance or that is permitted for direct addition to food for human consumption under 21 CFR 172.320 as an amino acid. Such neutralizing agents include sodium hydroxide, among others.

BACKGROUND OF THE INVENTION

Hydroalcoholic hand sanitizing gels have found increasing use by consumers and in institutional facilities such as schools, hospitals, and restaurants. Their advantages include the ability to instantly kill germs and bacteria on the hands. Soap and water are not required. The hydroalcoholic gels can be formulated to provide conditioning and moisturizing benefits, as well as a pleasant after-feel on the hands.

High alcohol sanitizing gels are known in the art. They typically contain from about 60 to about 70 percent alcohol. They may also contain emollients, moisturizers, conditioners, fragrances, dyes, and colorants. Thickening agents are used to obtain a gelled composition. The thickening agents employed must be capable of thickening the high alcohol content gel compositions without leaving a residue on the skin that is overly sticky. Prior art thickening agents include addition polymers of acrylic acid crosslinked with an unsaturated polyfunctional agent such as a polyallyl ether of sucrose. These carboxy vinyl polymers are described in U.S. Pat. Nos. 2,798,053 and 3,133,865, and have the CTFA (Cosmetic, Toiletry and Fragrance Association) adopted name of "carbomer." Carbomers are the preferred thickening agents because they are cost-effective and aesthetically pleasing. Carbomers have the ability to thicken compositions comprising over 90 percent ethanol and/or isopropyl alcohol. They also have the ability to produce clear systems with shear thinning rheology for effective dispensing and application to the hands.

The key to formulating hydroalcoholic gels with carbomers is choosing the correct neutralizing agent. The neutralizing agent neutralizes at least a portion of the carboxyl groups within the carbomer molecules, converting the acidic carbomer to a water soluble salt, and facilitating optimum thickening. The prior art, however, teaches that sodium hydroxide, and other well known neutralizers do not work in high alcohol hydroalcoholic systems, due to the low level of available water, and the low solubility of the carbomer salt. Table 1 summarizes the neutralizing agents for various alcohol levels recommended in. TDS-237, entitled "Neutralizing Carbopol™ and Pemulen™ Polymers in Aqueous and Hydroalcoholic Systems," from B.F. Goodrich (1998). As shown in Table 1, sodium hydroxide and potassium hydroxide are only recommended for hydroalcoholic systems comprising up to about 20% and about 30%, respectively, alcohol. Likewise, U.S. Pat. No. 4,956,170 to Lee teaches that sodium hydroxide, triethanolamine, monoethanolamine, and dimethyl stearylamine are not compatible as neutralizing agents because they do not adequately form a gel of desirable viscosity in a 60% ethanol composition. In fact, many neutralizing agents, including all of the GRAS neutralizing agents listed in 21 CFR 184, and all of the amino acids listed in 21 CFR 172.320 are known not to provide the desired viscosity in a 60% or greater alcohol composition as presently produced.

TABLE 1

Neutralizing agents for Hydroalcoholic Systems Recommended in Prior Art

| Maximum % Alcohol | Neutralizing agent |
|---|---|
| 20 | Sodium Hydroxide |
| 30 | Potassium Hydroxide |
| 60 | Triethanolamine |
| 60 | Tris Amino |
| 80 | Amino Methyl Propanol (AMP-95 ®) |
| 90 | Neutrol TE |
| 90 | Diisopropanolamine |
| 90 | Triisopropanolamine |
| >90 | Ethomeen C-25 |

An antimicrobial skin sanitizing composition comprising a high concentration of alcohol, a thickening agent and a neutralizing agent that is designated by the FDA as Generally Recognized As Safe (GRAS) under 21 CFR 184 or that is permitted for consumption as an amino acid under 21 CFR 172.320, would be desirable.

SUMMARY OF INVENTION

It is therefore, an object of the present invention to provide a high alcohol antimicrobial skin sanitizing composition comprising one or more hydroxides, and particularly NaOH, as a neutralizing agent that is designated by the FDA as Generally Recognized As Safe (GRAS) under 21 CFR 184.

It is another object of the present invention to provide a high alcohol antimicrobial skin sanitizing composition comprising one or more amino acids as a neutralizing agent that is permitted for direct addition to food for human consumption under 21 CFR 172.320.

It is still another object of the present invention to provide a method for preparing a high alcohol antimicrobial skin sanitizing composition that employs such a neutralizing agent.

It has now been found that neutralizing agents such as sodium hydroxide, which have been designated by the FDA as GRAS, as well as the amino acids designated under 21 CFR 172.320, can be used as neutralizers for high alcohol antimicrobial skin sanitizing compositions. More particularly, it has been found that, by carefully controlling the pH and adjusting the order of addition of ingredients, such high alcohol sanitizing gels having acceptable viscosity can be prepared.

At least one or more of the foregoing objects, together with the advantages thereof over the known art relating to antimicrobial skin sanitizing compositions, which shall become apparent from the specification that follows, are accomplished by the invention as hereinafter described and claimed.

In general, the present invention provides an antimicrobial skin sanitizing composition comprising at least about 60 percent of an aliphatic alcohol having from 1 to 4 carbon atoms, from about 0.1 to about 5 weight percent of a thickening agent, and an effective amount of a neutralizer designated by the FDA as a direct food substance that is Generally Recognized As Safe or as an amino acid permitted for direct addition to food for direct human consumption, to neutralize the thickening agent.

The present invention also provides a method for preparing a high alcohol skin sanitizing composition, the method comprising: dispersing a thickening agent in water to form a thickener dispersion; adjusting the pH of the thickener dispersion by using a neutralizer to form a gel; and subsequently adding an aliphatic alcohol having from 1 to 4 carbon atoms to the gel to form a sanitizing composition comprising at least about 60 percent by weight alcohol.

PREFERRED EMBODIMENT FOR CARRYING OUT THE INVENTION

The present invention is directed toward an antimicrobial sanitizing composition comprising an alcohol, a thickener containing a thickening agent, and a neutralizer containing a neutralizing agent. The neutralizing agent of the present invention however is one that has been designated by the FDA as a direct food substance affirmed to be Generally Recognized As Safe under 21 CFR 184, or that is an amino acid permitted for direct addition to food for human consumption under 21 CFR 172.320. The sanitizing composition has been formulated for preferably topical application to skin, and more particularly, to the hands.

Alcohols of the type employed in skin sanitizing compositions of the present invention are used for their antimicrobial properties. For example, high alcohol compositions kill gram-positive and gram-negative bacteria, fungi, and many other microbes. The potent activity of alcohol against microorganisms is believed to be due to denaturation of proteins and enzymes and dehydration. Generally, a concentration of alcohol of at least about 60 percent by weight, and more preferably, at least about 65 percent by weight of the composition is an effective amount for providing antimicrobial activity to the composition, although more or less alcohol may be required in certain instances, depending particularly on other ingredients and/or the amounts thereof employed in the composition. However, it will be appreciated that if lesser amounts of alcohol are used, an additional antimicrobial agent is typically employed. In a preferred embodiment, the present invention is devoid of any other antimicrobial agents in amounts greater than about 2 percent by weight. Thus, the skin sanitizing composition of the present invention preferably comprises at least about 60 percent by weight, more preferably, from about 60 to about 90 percent by weight alcohol, and even more preferably, from about 65 to about 90 percent by weight alcohol.

The alcohol employed in the skin sanitizing composition of the present invention is preferably a lower alkanol. Suitable alcohols include, but are not necessarily limited to, aliphatic alcohols containing from 1 to about 4 carbon atoms. Specific examples of suitable alcohols include methanol, ethanol, propanol, isopropanol, butanol, isobutanol and tertiary butanol. Ethanol is the most preferred alcohol for the preferred embodiment of the present invention. The alcohol may be either pure alcohol or denatured alcohol.

It is noted that the composition may optionally contain certain other sanitizing or antimicrobial agents in addition to alcohol which might provide some residual antimicrobial efficacy. These other antimicrobial agents include, but are not limited to, triclosan, also known as 5-chloro-2(2,4-dichlorophenoxy)phenol and available from Ciba-Geigy Corporation under the trade name Irgasan; chloroxylenol, also known as 4-chloro-3,5-xylenol and available from Nipa Laboratories, Inc. under the trade names Nipacide MX or PX; hexetidine, also known as 5-amino-1,3-bis(2-ethylhexyl)-5-methyl-hexahydropyrimidine; chlorhexidine salts including chlorhexidine gluconate and the salts of N,N"-bis(4-chlorophenyl)-3,12-diimino-2,4,11,14-tetraazatetradecanediimidi amide; 2-bromo-2-nitropropane-1; 3-diol, benzalkonium chloride; cetylpyridinium chloride; alkylbenzyldimethylammonium chlorides; iodine; phenol derivatives, povidone-iodine including polyvinylpyrrolidinone-iodine; parabens; hydantoins and derivatives thereof, including 2,4-imidazolidinedione and derivatives of 2,4-imidazolidinedione as well as dimethylol-5,5-dimethylhydantoin; phenoxyethanol; cis isomer of 1-(3-chloroallyl)-3,5,6-triaza-1-azoniaadamantane chloride, also known as quaternium-15 and available from Dow Chemical Company under the trade name Dowcil 2000; diazolidinyl urea; benzethonium chloride; methylbenzethonium chloride; and mixtures thereof. Most preferred of these antimicrobial agents are triclosan, chloroxylenol and chlorhexidine gluconate. These antimicrobial agents are used in amounts that do not affect the essential nature of the invention, and, as such, they may be viewed as preservatives rather than active ingredients. They are preferably used in amounts of from about 0 to about 1 percent by weight.

The thickening agent employed in the skin sanitizing composition of the present invention may be any water-dispersible polymeric gelling agent known in the art. The thickening agent assists in stabilizing the formulation to avoid early crystallization. A preferred type of thickening agent is a carbomer, which is a carboxy vinyl polymer. Carbomer thickening agents are commercially available under the trade names Carbopol® 934, 940, 941, 951, ETD 2020, ETD 2010, ETD 2001, and Ultrez™ from Noveon, Inc. of Cleveland, Ohio. Other thickening polymers and gums may be used according to their compatibility with the hydroalcoholic system. Examples of other suitable gelling agents include cellulosic ether polymers sold by Dow Chemical as Methocel® and hydroxymethyl, hydroxyethyl and hydroxypropyl cellulose gums sold under the mark Aqualon.®

The amount of thickening agent employed in the skin sanitizing composition of the present invention will vary depending upon the type of thickening agent, amount of alcohol, type of alcohol, and other factors, but in general, it is preferred to use from about 0.1 to about 5 percent by weight thickening agent, based upon the total weight of the sanitizing composition.

As used throughout this specification, the term "thickening agent" refers to a water-dispersible polymeric gelling agent, as described above. The term "thickener dispersion" refers to a thickening agent dispersed in a liquid, such as water. Carbopol® polymers are supplied as dry, tightly coiled acidic molecules. Once dispersed in water, the molecules begin to hydrate and partially uncoil. The most common way to achieve maximum thickening from Carbopol® polymers is by neutralizing the acidic polymer and converting it to a salt. Optimum thickening results are attained when from about 15 to about 100 percent of the carboxyl groups present in the acrylic acid polymer are neutralized. Preferably at least about 50 percent of the carboxyl groups are neutralized. For purposes of this specification, when neutralizing the thickening agent or the thickener is described or referred to herein, this should be understood to refer to neutralizing a sufficient portion of the carboxyl groups of the thickening agent. A sufficient portion is preferably about 15 to about 100 percent of the carboxyl groups present in the thickening agent, and more preferably at least about 50 percent of the carboxyl groups present in the thickening agent.

Neutralizing agents well known in the art include, triethanolamine, sodium hydroxide, monoethanolamine and dimethyl stearylamine. Other neutralizing agents are also known, such as $HO(C_mH_{2m})_2NH$, where m has the value of from 2 to 3, and aminomethyl propanol, aminomethyl propanediol, and ethoxylated amines, such as PEG-25 cocamine, polyoxyethylene (5) cocamine (PEG-5 cocamine), polyoxyethylene (25) cocamine (PEG-25 cocamine), polyoxyethylene (5) octadecylamine (PEG-5 stearamine), polyoxyethylene (25) octadecylamine (PEG-25 stearamine), polyoxyethylene (5) tallowamine (PEG-5 tallowamine), polyoxyethylene (15) oleylamine (PEG-15 oleylamine), polyethylene (5) soyamine (PEG-5 soyamine), and polyoxyethylene (25) soyamine (PEG-15 soyamine). A number of these are commercially available under the trade name of Ethomeen from Akzo Chemie America, Armak Chemicals of Chicago, Ill.

The prior art teaches that the correct neutralizing agent must be carefully selected based upon the amount of alcohol that is to be gelled. For example, U.S. Pat. No. 4,956,170 teaches that triethanolamine, sodium hydroxide, monoethanolamine, and dimethyl stearylamine are not compatible as neutralizing agents for high (>60%) alcohol compositions because they do not cause the thickening agent to gel the composition to the desired viscosity. Additionally, technical bulletins for Carbopol® polymers teach that sodium hydroxide can only be used in compositions containing 20 percent by weight or less alcohol, and potassium hydroxide can only be used in compositions containing 30 percent by weight or less alcohol. These bulletins state that, if the wrong neutralizing agent is used, the salt of the Carbopol® polymer will precipitate out because it is no longer soluble in the hydroalcoholic blend.

Surprisingly, it has now been found that, by controlling the pH and the order in which the ingredients of the skin sanitizing composition are combined, sodium hydroxide as well as other neutralizing agents identified below are effective neutralizing agents for compositions containing high amounts of alcohol. Advantageously, the neutralizing agents including sodium hydroxide have all been either designated by the FDA Generally Recognized As Safe (GRAS) for direct food addition or been designated by the FDA as an amino acid permitted for direct addition to food for human consumption. Therefore, neutralizers of the present invention may contain essentially any neutralizing agent which has been so designated by the FDA. Such neutralizing agents include various hydroxides selected from the group consisting of sodium hydroxide, potassium hydroxide, ammonium hydroxide, magnesium hydroxide, and precursors thereof as well as various amino acids selected from the group consisting of arginine, cysteine, and thiamine.

Neutralizers containing sodium hydroxide or sodium hydroxide precursors are the preferred neutralizers for the skin sanitizing composition of the present invention. Solutions of sodium hydroxide in water are non-limiting examples of neutralizers containing sodium hydroxide.

The neutralizer is employed in an effective amount to neutralize a portion of the carboxyl groups of the thickening agent, and produce the desired pH range. The pH of unneutralized thickening agent dispersed in water is generally acidic. For example, the pH of Carbopol polymer dispersions is approximately in the range of 2.5 to 3.5, depending upon the polymer concentration. An effective amount of neutralizer, when added to the thickener dispersion, adjusts the pH to a desired range of about 4.1 to 4.8 and more preferably, to about 4.2 to 4.6. The amount of neutralizer necessary to effect this pH range will vary depending upon factors such as the type of thickening agent, the amount of thickening agent, etc. However, in general, amounts less than 1 percent by weight and preferably ranging from about 0.001 to about 0.3 percent by weight of the neutralizing agent are considered sufficient and effective. In one preferred embodiment, the skin sanitizing composition of the present invention comprises from about 60 to about 90 percent by weight ethyl alcohol, from about 0.1 to about 5 percent by weight thickening agent, and from about 0.001 to about 0.2 percent by weight sodium hydroxide.

Although alcohol is generally recognized as a very effective antimicrobial agent and is often noted as being relatively mild to the skin as compared to other active antimicrobial ingredients, continuous use of alcohol-based compositions, without protection, will ultimately dry out the skin, causing it to chap or crack. Therefore, it may be desirable to provide moisturizing properties to the skin, preferably at the same time the alcohol is being utilized. Thus, moisturizers may be added to the composition of the present invention to provide skin conditioning benefits and decrease water loss from the skin, with the proviso that the moisturizing agent does not affect the essential nature of the invention.

More than one moisturizing agent may be used in the composition of the present invention, and may or may not provide other advantageous properties to the composition. For example, one or more moisturizing agents may have opacifying properties. Preferred opacifying moisturizers are disclosed in U.S. Pat. No. 6,333,039, hereby incorporated by reference in its entirety. Preferred opacifying moisturizers are selected from the group consisting of polyethylene, polypropylene, and sodium styrene-based copolymers.

These opacifying moisturizing agents are preferably used in effective amounts suitable for making the resultant sanitizing composition uniformly opaque upon proper mixing and to reduce the rate of water loss from the skin upon application of the sanitizing composition. Typically, from 0 percent by weight to about 5 percent by weight of the opacifying moisturizer is employed.

Other moisturizing agents which are not opacifying agents may also be used in the present invention. Examples of such moisturizers include glycerin, polyhydric alcohols such as sorbitol, hydrolyzed proteins, urea, hydrolyzed starch, hydroxy acids such as lactic acid and fruit acids and salt derivatives thereof, pyrrolidone carboxylic acid, aloe vera gel, cucumber juice, mineral oils, squalene, and tocopherol. Preferably, these moisturizing agents are used in amounts effective for softening or moisturizing the skin, those amounts typically ranging from 0 to about 2 percent by weight. Glycerin is preferred. Glycerin is commonly used in personal care products for its humectant properties, but it is also recognized for its excellent moisturizing and softening properties.

Also suitable as moisturizing agents are essentially non-volatile silicone fluids, such as a polyallyl siloxane, a polyaryl siloxane, a polyallylaryl siloxane or a polyether siloxane copolymer. An effective amount of these silicone fluids, when used to soften and moisten the skin, is typically from about 0 to about 10 percent by weight. Examples of essentially non-volatile polyalkyl siloxane fluids useful for the present invention include dimethicone and dimethiconol, available under the trade name Dow Corning 1403 Fluid.

The sanitizing composition of the present invention may contain additional optional ingredients that render the composition more easily formulated, or more aesthetically and/or cosmetically acceptable, with the proviso that the optional ingredients do not affect the essential nature of the invention. Examples of such optional ingredients are known in the art, and include, but are not limited to, preservatives, emollients, lubricity agents, perfumes, opacifiers, and dyes. Generally, the effective amounts of these ingredients are known to those skilled in the art, and are typically on the order of less than 1 percent by weight.

Emollients are often used to impart a smooth and soft feeling to the skin surface in much the same way as the moisturizers discussed hereinabove. However, emollients impart a smooth and soft feel to the skin without measurably affecting the skin hydration level and or the skin lipid barrier. Examples of emollients include vegetable triglycerides, such as avocado oil, olive oil, and sunflower seed oil, and organic acid esters such as sorbitan oleate, myristyl myristate, isopropyl myristate, and glyceryl oleate.

Preservatives prevent microbial spoilage. Examples of preservatives include the optional antimicrobial agents described hereinabove, used in minor amounts. Other examples of preservatives include, but are not limited to, iodopropynyl butylcarbamate, imidazolidinyl urea, methylchloroisothiazolinone and methylisothiazolinone.

Lubricity agents aid in creating a soft and smooth feeling as the sanitizing composition is applied to the skin. An example of a lubricity agent useful in the present invention is a benzoic acid ester of a $C_{12}$-$C_{15}$ alcohol, such as is available under the trade name Finsolv TN. Other useful lubricity agents include volatile silicones, such as cyclomethicone tetramer and pentamer, which is available from Dow Corning as Dow Corning 244 or 245 Fluids) and non-volatile silicones, such as stearyl dimethicone, which is available from Dow Corning as Dow Corning 2503 Cosmetic Wax.

Any of the opacifiers, perfumes, and dyes known in the art as useful in the formulation of skin sanitizing compositions may be employed. The balance of the composition may be water. Water acts as a vehicle to ensure even distribution of the composition on the skin. As stated above, it has now been found that, by controlling the pH and the order in which the ingredients of the skin sanitizing composition are combined, sodium hydroxide and the other neutralizing agents are effective neutralizing agents for compositions containing high amounts of alcohol.

Accordingly, the present invention provides a method for preparing a high alcohol skin sanitizing composition. The process differs from prior art methods in that the formulation of the composition of the present invention does not add alcohol prior to the addition of a neutralizing agent. Instead, a thickening agent such as a carbomer is dispersed in water, allowed to hydrate at ambient temperature, and then mixed to form a thickener dispersion. Next, instead of adding alcohol, the pH of the thickener dispersion is adjusted by adding a neutralizer to form a gel. The pH is adjusted to about 4.1 to about 4.8, much more acidic than the pH found in prior art compositions.

Once the pH is established, then the aliphatic alcohol is added to the gel to form the sanitizing composition. This may be done using any method known in the art but preferably is done by mixing with agitation.

Preferably, the sanitizing composition includes at least about 60 percent by weight of the aliphatic alcohol. The viscosity of the sanitizing composition may be from about 1,000 to about 65,000 centipoise (cps) (Brookfield heliopath, RVT-D, speed 10, 70° F.). More preferably, the viscosity of the sanitizing composition is from about 3,000 to about 15,000 cps.

It will also be appreciated that the sanitizing composition of the present invention will have a density of at least 0.8 g/ml and preferably between about 0.8 g/ml and 0.9 g/ml. Thus, this composition is not a mousse and other extremely porous composition, and yet is less dense than water.

Any of the equipment or methods known in the art may be used to agitate and mix the components in the method of the present invention. One embodiment of the present invention has used an APV Crepaco sweep agitator. Optional components, such as those discussed above, may be added to the gel, to the sanitizing composition, or may be premixed with the alcohol prior to addition to the neutralized dispersion.

In order to demonstrate practice of the present invention, a sample of the preferred sanitizing composition was prepared by first dispersing, by way of sprinkling, approximately 3.6 grams of the thickening agent, into about 336 grams of process water. The polymer was allowed to hydrate at ambient temperature for about 15 minutes, and then was mixed thoroughly with the agitator for another 15 minutes.

The pH of the dispersion was adjusted to between 4.1 and 4.8 by addition of about 0.9 grams of a 25 percent solution of sodium hydroxide in water. The resulting gel had a viscosity of from about 35,000 to about 125,000 cps. After mixing, approximately 655 grams of specially denatured alcohol (190 proof) was then added to the gel. Next, about 2 grams of fragrance, about 2.5 grams of glycerin, about 0.01 grams of propylene glycol, and 0.001 grams of vitamin E were added. The mixture was agitated with an Eurostar Lab Mixer until uniform and then poured into suitable containers.

The resultant sanitizing composition was tested in vitro to determine its effectiveness against particular strains of several different bacteria. The challenged bacteria included one strain of *Staphylococcus aureus* deposited and available to the scientific public from the American Type Culture Collection (ATCC), Rockville, Md., under Accession No. 33591; one strain of *Serratia marcescens* available to the scientific public from the ATCC under Accession Number 14756; one strain of *Escherichia coli*, available to the scientific public from the ATCC under Accession Number 11229; one strain of *Pseudomonas aeruginosa* available to the scientific public from the ATCC under Accession Number 15442; and one strain of *Candida albicans* available to the scientific public from the ATCC under Accession Number 10231. In addition, high alcohol prior art compositions were also tested. These high alcohol prior art compositions included non-GRAS, non-amino acid neutralizing agents such as AMP-95. It will also be appreciated that the prior art compositions were formulated using the prior art method of mixing the carbomer, then the alcohol, and then neutralizing with a known neutralizing agent such as AMP-95. The pH of the prior art compositions were determined to be around 7.0.

A 15 second efficacy screen was then conducted. Specifically, each bacteria was rehydrated and incubated and made into a bacterial suspension. The concentration of each bacterial suspension is set forth at the bottom of Table II. Table II reports the antibacterial efficacy of reduction of colony forming units (CFU's) of the challenged bacteria in terms of percent reduction for a 15 second exposure screen performed against these bacteria. As noted, in percentages, the composition reduced the number of CFU's by greater than 99.999% (a 5 log reduction).

TABLE II

ANTIMICROBIAL EFFICACY
15 SECOND EXPOSURE KILL EVALUATION

| High Alcohol Product | Staphylococcus aureus ATCC #33591 | Serratia marcescens ATCC #14756 | Escherichia coli ATCC #11229 | Pseudomonas aeruginosa ATCC #15442 | Candida albicans ATCC #10231 |
|---|---|---|---|---|---|
| | | | Percent Reduction | | |
| PRIOR ART | >99.999 | >99.999 | >99.999 | >99.999 | >99.999 |
| PRIOR ART | >99.999 | >99.999 | >99.999 | >99.999 | >99.999 |
| INVENTION | >99.999 | >99.999 | >99.999 | >99.999 | >99.999 |
| Challenged, Bacteria, CFU/mL | $2.38 \times 10^5$ | $3.60 \times 10^5$ | $1.52 \times 10^5$ | $3.20 \times 10^5$ | $1.68 \times 10^5$ |

Thus, it is clear that the resultant sanitizing composition of the present invention is effective in killing bacteria and other harmful microorganisms without harming the skin on the hands. Moreover, because the composition employs sodium hydroxide as the neutralizing agent, at least the neutralizing agent of the composition is generally recognized as safe by the Food and Drug Administration (FDA).

Thus it should be evident that the method of the present invention is highly effective in preparing a high alcohol skin sanitizing composition comprising a hydroxide or an amino acid as a neutralizing agent. The composition of the present invention is particularly suited for disinfecting skin, and more particularly hands, but is not necessarily limited thereto. The composition and method of the present invention can be used separately with other equipment, methods and the like, as well as for the manufacture of other materials.

Based upon the foregoing disclosure, it should now be apparent that the use of the composition and method described herein will carry out the objects set forth hereinabove. It is, therefore, to be understood that any variations evident fall within the scope of the claimed invention and thus, the selection of specific component elements can be determined without departing from the spirit of the invention herein disclosed and described. Thus, the scope of the invention shall include all modifications and variations that may fall within the scope of the attached claims.

What is claimed is:

1. A method of making an alcohol skin sanitizing composition consisting of:
    a) dispersing about 0.1 to about 5 weight percent of a carbomer polymer in water; then
    b) adding sodium hydroxide, in an amount to neutralize at least 50 percent of the carboxyl groups present in said carbomer polymer to obtain a gel having pH between about 4.1 and 4.8 and a viscosity of from about 35,000 to about 125,000 centipoises; and then
    c) adding ethanol to said gel wherein the amount of ethanol is at least 60 percent by weight of said composition to reduce the viscosity to from about 1000 to about 65,000 centipoises at 70 degrees Fahrenheit, wherein the resultant composition is a clear gel.

\* \* \* \* \*